United States Patent [19]

Reiffenrath et al.

[11] Patent Number: 5,387,689
[45] Date of Patent: Feb. 7, 1995

[54] CHIRAL VALEROLACTONE DERIVATIVES

[75] Inventors: Volker Reiffenrath, Rossdorf; Ulrich Finkenzeller, Plankstadt, both of Germany

[73] Assignee: Merck Patent Gesellschaft Mit Beschrankter Haftung, Darmstadt, Germany

[21] Appl. No.: 118,652

[22] Filed: Sep. 10, 1993

[30] Foreign Application Priority Data

Sep. 10, 1992 [DE] Germany .................. 4230288

[51] Int. Cl.⁶ ................................ C07D 309/02
[52] U.S. Cl. .................. 546/268; 544/335; 548/136; 549/291; 549/292
[58] Field of Search ............. 549/287, 291, 292; 544/335; 546/268; 548/136

[56] References Cited

FOREIGN PATENT DOCUMENTS 409066 7/1990 European Pat. Off. ............ 549/287

OTHER PUBLICATIONS

Brienne et al., *Tetrahedron Letters*, No. 28, pp. 2349–2352, Jul. 1975.
Hu et al., *Journal of Chromatography*, vol. 482, No. 1, pp. 227–233, Nov. 17, 1989.
Chemical Abstracts, vol. 114, No. 17, Abstract 164, 265 p., pp. 783–784, Apr. 29, 1991, Ulrike et al.
Katagiri et al., *Biochemical and Biophysical Research Communications*, vol. 184, No. 1, pp. 154–159, Apr. 15, 1992.

Primary Examiner—C. Warren Ivy
Assistant Examiner—Zinna N. Davis
Attorney, Agent, or Firm—Millen, White, Zelano, & Branigan

[57] ABSTRACT

The invention relates to chiral valerolactone derivatives of the formula I

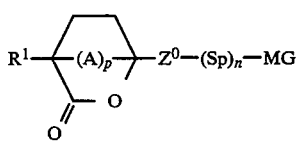

wherein $R^1$ is $C_{1-18}$ alkyl in which one or two non-adjacent $-CH_2$ groups are optionally replaced by $-O-$, $-CO-O-$, $-O-CO-$ or $-S-$, A is $-H_2-$, $-C-(CH_3)_2-$ or $-CH_2CH_2$, Sp is a spacer, which optionally contains a chiral carbon atom, $Z^0$ is $-COO-$, $-CH_2O-$, $-CH_2CH_2-$, $-C\equiv C-$ or $-CH=CH-$, MG is a mesogenic group, and n and p are each 0 or 1, and the use thereof as components of liquid-crystalline media for electrooptical displays.

9 Claims, No Drawings

CHIRAL VALEROLACTONE DERIVATIVES

SUMMARY OF THE INVENTION

The invention relates to chiral valerolactone derivatives of the formula I

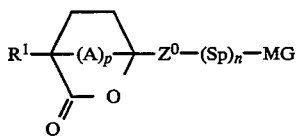

in which
- $R^1$ is alkyl having 1 to 18 carbon atoms, in which, in addition, one or two non-adjacent —$CH_2$— groups may be replaced by —O—, —CO—O—, —O—CO— or —S—,
- A is —$CH_2$—, —$C(CH_3)_2$— or —$CH_2CH_2$—
- Sp is a spacer, which may contain a chiral carbon atom,
- $Z^0$ is COO, $CH_2$O, $CH_2CH_2$, —C≡C— or —CH=CH—,
- MG is a mesogenic group, and
- n and p are each 0 or 1.

Particularly in the last decade, liquid crystals have been introduced into various industrial areas in which electro-optical and display-device properties are required (for example in watch, calculator and typewriter displays). These display devices are based on the dielectric alignment effects in the nematic, cholesteric and/or smectic phases of the liquid-crystalline compounds, where — caused by the dielectric anisotropy — the molecular long axis of the compounds adopts a preferential alignment in an applied electrical field. The usual response times in these display devices are too long for many other potential areas of application of liquid crystals. This disadvantage is particularly noticeable if a large number of pixels have to be addressed. Production costs of equipment containing relatively large screen areas, such as, for example, of video equipment, are then generally too high.

In addition to nematic and cholesteric liquid crystals, optically active smectic liquid-crystal phases have also been increasing in importance in the last few years.

Clark and Lagerwall have been able to show that the use of ferroelectric liquid-crystal systems in very thin cells gives opto-electrical switching or display elements which have response times up to a factor of 1000 quicker than conventional TN ("twisted nematic") cells (cf., for example, Lagerwall et al., "Ferroelectric Liquid Crystals for Displays", SID Symposium, October Meeting 1985, San Diego, Calif., USA). Due to these and other favorable properties, for example the possibility of bistable switching and the virtually viewing angle-independent contrast, FLCs are in principle highly suitable for the abovementioned areas of application, for example via matrix addressing.

For electro-optical switching and display elements, either compounds which form tilted or orthogonal smectic phases and are themselves optically active are required, or ferroelectric smectic phases can be induced by doping compounds which, although forming smectic phases of this type, are not themselves optically active, with optically active compounds. The desired phase should be stable over the broadest possible temperature range.

In order to achieve good contrast in electro-optical components, a uniform planar alignment of the liquid crystals is necessary. Good alignment in $S^*_A$ and $S^*_C$ phases can be achieved if the phase sequence of the liquid-crystal mixture is, with decreasing temperature:

isotropic→$N^*$→$S^*_A$→$S^*_C$

The prerequisite is that the pitch of the helix in the N* phase is very large (greater than 10 μm) or, still better, is fully compensated (see, for example, T. Matsumoto et al., p. 468–470, Proc. of the 6th Int. Display Research Conf., Japan Display, Sep. 30 –Oct. 2, 1986, Tokyo, Japan; M. Murakami et al., ibid., p. 344-347). This is achieved by treating the chiral liquid-crystal mixture which has, for example, a left-handed helix in the N* phase with a further optically active dope which induces a right-handed helix, in such amounts that the helix is just compensated.

The disadvantage of this process is that not only is the pitch compensated, but the spontaneous polarization is also affected.

There is therefore a great demand for optically active dopants which induce high spontaneous polarisation in an achiral base mixture, do not simultaneously affect the phase range of the $S_c^*$ phase, or only do so to a small extent, and simultaneously have a large pitch.

It has now been found that chiral valerolactone derivatives of the formula I cause high spontaneous polarization values together with a virtually compensated pitch.

The general formula of EP 0 409 066 covers some of the compounds of the formula I according to the invention (p=0, but no compounds are described therein in which the wing group $R^1$ is linked directly in the 2-position to the valerolactone ring.

Neither is there any indication that such compounds cause high spontaneous polarization at the same time as virtually compensated helical pitch.

The invention therefore relates to the chiral 2,6-difluorobenzene derivatives of the formula I.

Preferred embodiments are:
a) Chiral valerolactone derivatives of the formula I, in which $Z^0$ is COO.
b) Chiral valerolactone derivatives of the formula I, in which p is 1.
c) Chiral valerolactone derivatives of the formula I1,

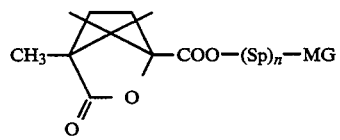

in which Sp, MG and n are as defined above.
d) Chiral valerolactone derivatives of the formula I, in which MG is a radical of the formula II

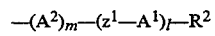

—$(A^2)_m$—$(z^1$—$A^1)_l$—$R^2$     II in which
- $R^2$ is an alkyl or alkenyl radical, each having 1 to 18 carbon atoms, which is unsubstituted or at least monosubstituted by halogen or monosubstituted by cyano and in which one or two non-adjacent —CH$_2$—groups may be replaced by —O—, —CO—O—, —O—CO— or —S—,
or is a radical of the formula

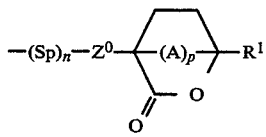

in which Sp, Z$^0$, A, R$^1$, n and p are as defined above,
A$^1$ and A$^2$ are each, independently of one another, 1,4-phenylene which is unsubstituted or substituted by one or two fluorine atoms and in which one or two CH groups may be replaced by N, or are 1,4-cyclohexylene which is unsubstituted or substituted by a cyano group and in which one or two CH$_2$ groups may be replaced by O or S, or are thiadiazole-2,5-diyl or 1,4-bicyclo[2,2,2]octylene,
Z$^1$ is —CO—O—, —O—CO—, —CH$_2$O—, —OCH$_2$—, —CH$_2$CH$_2$—, —C≡C— or a single bond,
l is 0, 1 or 2,
m is 1 or 2, and
(l+m) is 1, 2 or 3.
e) Chiral valerolactone derivatives of the formula I, in which at least one of the groups A$^1$ and A$^2$ is selected from the formulae 1 to 7:

 1

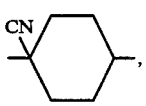 2

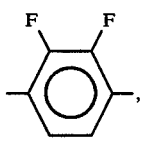 3

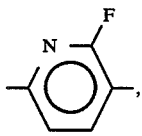 4

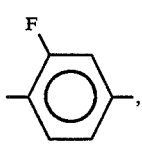 5

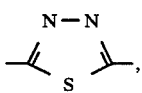 6

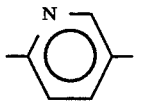 7 f) Chiral valerolactone derivatives of the formula I in which Sp is a group of the formula III

 III in which
q and s are each, independently of one another, an integer between 0 and 6,
r is 0 or 1, and
W is halogen, alkyl having 1 to 6 carbon atoms or phenyl,
with the proviso that the sum of q, s and r is at least 1,
in particular in which Sp is a group of the formula III1

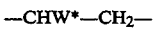 III1 in which W is as defined above.
The invention furthermore relates to liquid-crystalline media containing at least two liquid-crystalline components, characterised in that they contain at least one compound which contains a structural unit of the formula IV

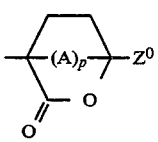 IV in which A, Z$^0$ and p are as defined in claim 1, in particular in which p is 1 and Z$^0$ is COO, or a liquid-crystalline medium which contains at least one valerolactone derivative of formula I. The invention furthermore relates to electro-optical displays containing a liquid-crystalline medium of this type.
Further preferred embodiments are:
g) Chiral derivatives in which R$^2$ is a radical of the formula V

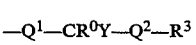 V in which
Q$^1$ and Q$^2$ are a C$_{1-8}$-alkylene group in which, in addition, one or two CH$_2$ groups may be replaced by —O—, and/or —S— in such a way that two heteroatoms are not adjacent,
R$^0$ is H or a C$_{1-6}$-alkyl group which is different from Y,
Y is CH$_3$, halogen, CF$_3$, CF$_2$H, CH$_2$F or CN,
R$^3$ is C$_{1-6}$-alkyl,
C* is a chiral carbon atom with four different substituents,
where the groups R$^0$, Y and —Q$^2$—R$^3$ are in each case different from one another;
h) chiral derivatives, in which R$^2$ is a radical of the formula VI

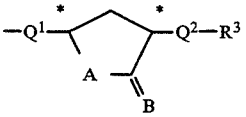 VI in which
Q$_1$, Q$^2$ and R$^3$ are as defined above, and
A is O, S or NH and
B is H$_2$, CH$_2$, O or S.

The invention also relates to chiral tilted smectic liquid-crystalline media containing at least one compound of the formula I, in particular a ferroelectric liquid-crystalline medium containing
- an achiral smectic component S, which contains at least one achiral smectic liquid-crystalline compound, and
- a chiral component D containing at least one chiral dopant where a chiral dopant is a compound of the formula I.

The invention furthermore relates to electrooptical display elements which contain phases of this type, in particular a liquid-crystalline, switching and display device of this type containing a ferroelectric liquid-crystalline medium, outer plates, electrodes, at least one alignment layer and optionally additional auxiliary layers, where the ferroelectric medium containing at least one compound of the formula I is a medium according to claim 7.

The term mesogenic group is known to persons skilled in the art (for example H. Kelker, H. Hatz, Handbook of Liquid Crystals) and denotes a rod-like radical comprising ring members, optionally bridging members and wing groups.

Above and below, $R^1$, $R^2$, $R^0$, A, $A^1$, $A^2$, Sp, $Q^1$, $Q^2$, W, Y, X, $X^1$, $Z^0$, $Z^1$, l, m, q, r, s and p are as defined above, unless expressly stated otherwise. Above and below, Val denotes a valerolactone group of the formula

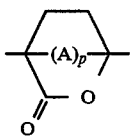

IV

Accordingly, the compounds of the formula I cover, in particular, compounds of the sub-formulae Ia to Il:

| | |
|---|---|
| $R^1$-Val-$Z^0$-$A^2$-$R^2$ | Ia |
| $R^1$-Val-$Z^0$-Sp-$A^2$-$R^2$ | Ib |
| $R^1$-Val-$Z^0$-$A^2$-$A^1$-$R^2$ | Ic |
| $R^1$-Val-$Z^0$-Sp-$A^2$-$A^1$-$R^2$ | Id |
| $R^1$-Val-$Z^0$-$A^2$$Z^1$-$A^1$-$R^2$ | Ie |
| $R^1$-Val-$Z^0$-Sp-$A^2$-$Z^1$-$A^1$-$R^2$ | If |
| $R^1$-Val-$Z^0$-$A^2$-$A^2$-$A^1$-$R^2$ | Ig |
| $R^1$-Val-$Z^0$-Sp-$A^2$-$A^2$-$A^1$-$R^2$ | Ih |
| $R^1$-Val-$Z^0$-$A^2$-$Z^1$-$A^1$-$A^1$-$R^2$ | Ii |
| $R^1$-Val-$Z^0$-Sp-$A^2$-$Z^1$-$A^1$-$A^1$-$R^2$ | Ij |
| $R^1$-Val-$Z^0$-Sp-$A^2$-$A^2$-$A^2$-$Z^1$-$A^1$-$R^2$ | Ik |
| $R^1$-Val-$Z^0$-$A^2$-$A^2$-$Z^1$-$A^1$-$R^2$ | Il |

Of these, those of the formulae Ia, Ib, Ic, Id and Ig are particularly preferred.

Compounds of the formulae above and below which contain branched wing groups $R^1$ are preferred. Branched groups of this type generally contain not more than two chain branches. $R^1$ is preferably a straightchain group or a branched group containing not more than one chain branch.

Preferred branched radicals are isopropyl, 2-butyl (=1-methylpropyl), isobutyl (=2-methylpropyl), tert-butyl, 2-methylbutyl, isopentyl (=3-methylbutyl), 2-methylpentyl, 3-methylpentyl, 4-methylpentyl, 2-ethylhexyl, 5-methylhexyl, 2-propylpentyl, 6-methylheptyl, 7-methyloctyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl and 3-oxa-4-methylpentyl.

The radical $R^1$ and in particular also the radical $R^2$ may alternatively be an optically active organic radical containing an asymmetrical carbon atom.

$R^1$ and $R^2$ are preferably alkyl or alkenyl having up to 15 carbon atoms. Particular preference is given to alkyl having 5 to 12 carbon atoms, i.e. pentyl, hexyl, heptyl, octyl, nonyl, decyl, undecyl and dodecyl. These groups may be straight-chain or branched, straight-chain alkyl groups being preferred. However, $R^2$ is preferably also methyl or branched alkyl containing a methyl branch, for example isopropyl.

Particular preference is given to compounds of the formula I in which $R^1$ is methyl, and $Z^0$ is preferably —COO—.

$Z^1$ is preferably in each case, independently of one another, —$CH_2CH_2$—, —C≡C— or a single bond, particularly preferably a single bond.

p is preferably 1, and n is preferably 0.

l is preferably 0 or 1, o is preferably 0 or 1, and n is preferably 1 or 2.

A is preferably —$C(CH_3)_2$—.

Of these compounds of the formula I and of the sub-formulae, those are preferred in which at least one of the radicals present therein has one of the preferred meanings indicated.

Some very particularly preferred smaller groups of compounds are those of the sub-formulae Ia1 to Ig6:

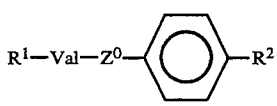

Ia1

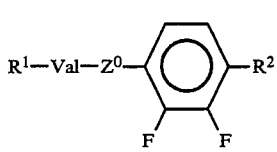

Ia2

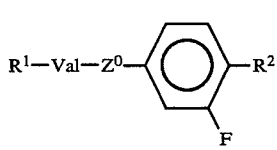

Ia3

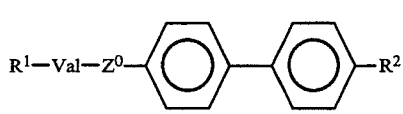

Ic1

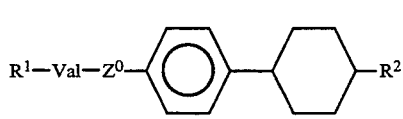

Ic2

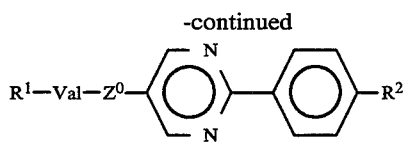 Ic3

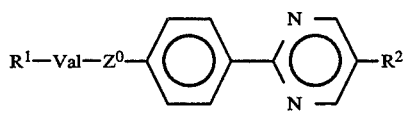 Ic3

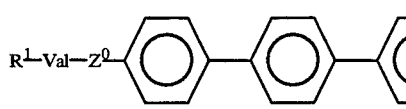 Ig1

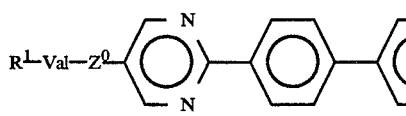 Ig2

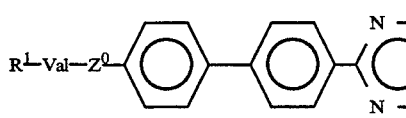 Ig3

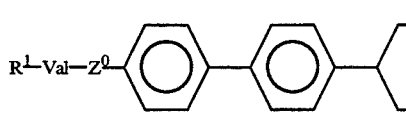 Ig4

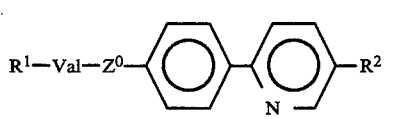 IG5

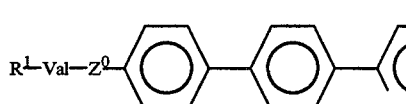 Ig6

Preferred chiral radicals of the formula V are those of the formulae Va to Vf:

 Va

 Vb

 Vc

 Vd

 Ve

 Vf in which, in each case,
m is 0 to 8, preferably 0 to 2, and
n is 2 to 14, preferably 2 to 10.

Preferred chiral radicals of the formula VI are those of the formulae VIa to VIb:

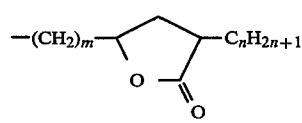 VIa

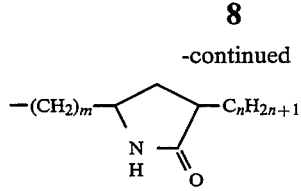 VIb in which, in each case,
m is 0 to 8, preferably 1, and
n is 2 to 14, preferably 2 to 10.

Further preferred chiral radicals $R^2$ are the radicals of the formulae VII and VIII:

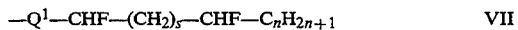 VII

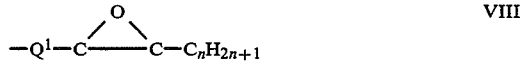 VIII in which
s is 0 to 6, and
n is 1 to 10.

The compounds of the formula I are prepared by methods known per se, as described in the literature (for example in the standard works, such as Houben-Weyl, Methoden der Organischen Chemie, [Methods of Organic Chemistry], Georg-Thieme-Verlag, Stuttgart), to be precise under reaction conditions which are known and suitable for said reactions. Use may also be made here of variants which are known per se, but are not described here in greater detail.

The compounds of the formula I, in which $Z^0$ is COO are prepared in accordance with Scheme 1:

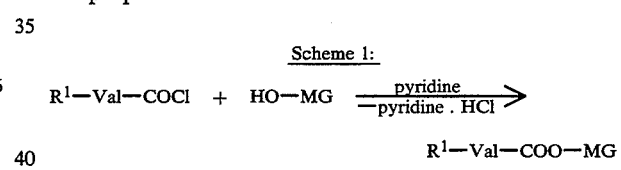

The compounds of the formula I in which $Z^0$ is $CH_2O$ are prepared in accordance with Scheme 2:

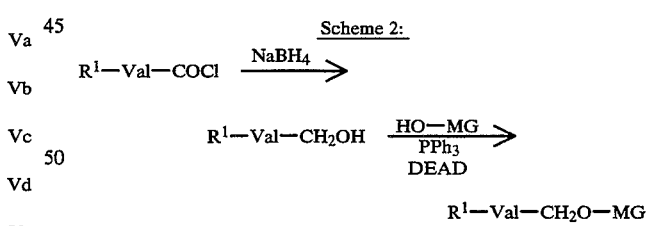

The compounds of the formula I in which $Z^0$ is CH=CH or $—CH_2CH_2—$ are prepared in accordance with Scheme 3:

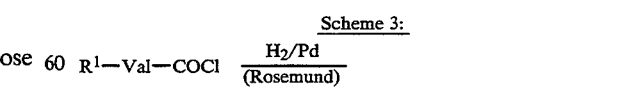

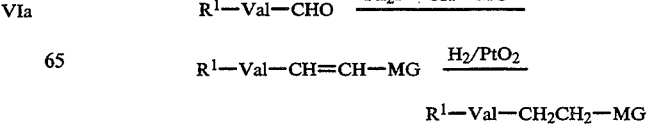

The compounds of the formula I in which Sp is a spacer of the formula IIIa are prepared in accordance with Scheme 4:

Scheme 4:

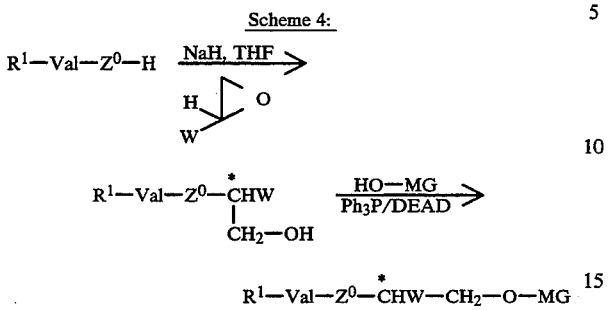

The media according to the invention contain at least one, preferably at least two, compounds of the formula I. The ferroelectric media according to the invention preferably contain an achiral smectic component S containing at least one achiral smectic compound, and a chiral compound D is at least one chiral dopant, where at least one chiral compound is a compound of formula I. Particular preference is given to chiral tilted smectic liquid-crystalline phases according to the invention whose achiral base mixture contains, in addition to compounds of the formula I, at least one other component having negative or low positive dielectric anisotropy. The chirality is preferably based partly or fully on chiral compounds of the formula I. These phases preferably contain one or two chiral compounds of the formula I. However, achiral compounds of the formula I (for example in the form of a racemate) can also be employed, in which case the chirality of the phase is caused by other optically active compounds. If chiral compounds of the formula I are used, mixtures having an enantiomer excess are suitable in addition to the pure optical antipodes. The abovementioned other component(s) of the achiral base mixture can make up from 1 to 50%, preferably from 10 to 25% of the base mixture.

The compounds of the formula I are also suitable as components of nematic liquid-crystalline phases, for example for preventing reverse twist.

Furthermore, the chiral valerolactone derivatives according to the invention can be used to prepare liquid-crystalline media for phase-change displays (for example Y. Yabe et al., SID 1991 Digest 261–264).

These liquid-crystalline media according to the invention comprise 2 to 25, preferably 3 to 15 components, including at least one compound of the formula I. The other constituents are preferably selected from smectic or smectogenic substances, in particular known substances, from the classes comprising the azoxybenzenes, benzylideneanilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphthalenes, 1,4-bis-cyclohexylbenzenes, 4,4'-bis-cyclohexylbiphenyls, phenyl or cyclohexylpyrimidines, phenyl- or cyclohexylpyridazines and their N-oxides, phenyl- or cyclohexyldioxanes, phenyl- or cyclohexyl-1,3-dithianes, 1,2-di-phenylethanes, 1,2-dicyclohexylethanes, 1-phenyl-2-cyclohexylethanes, optionally halogenated stilbenes, benzyl phenyl ethers, tolans and substituted cinnamic acids. The smectic compound S is based on achiral compounds of this type.

The most important compounds which are suitable as components of liquid-crystalline phases of this type can be characterized by the formula I'

$$R'—L—G—E—R''$$  I' in which L and E are each a carbocyclic or heterocyclic ring system from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, di- and tetrahydro-naphthalene, quinazoline and tetrahydroquinazoline, G is

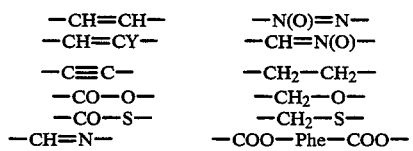

or a C—C single bond,

Y is halogen, preferably chlorine, or —CN, and R' and R" are alkyl, alkoxy, alkanoyloxy, alkoxycarbonyl or alkoxycarbonyloxy having 1 to 18, preferably 5 to 12, carbon atoms, or one of these radicals is alternatively F, —CF$_3$, —OCF$_3$ or CN.

In most of these compounds, R' and R' are alkyl or alkoxy groups of various chain length, the total number of carbon atoms usually being more than 12, preferably 12 to 20, in particular 13 to 18. However, other variants of the proposed substituents are also common. Many such substances or mixtures thereof are commercially available. All these substances can be prepared by methods which are known from the literature.

The liquid-crystalline media according to the invention contain about 0.1 to 99%, preferably 10 to 95%, of one or more compounds of the formula I. Additionally preferred liquid-crystalline phases are those which contain 0.1–40%, particularly 0.5–10%, of one or more compounds of the formula I.

As further mixture components of component S, preference is given to compounds of the following formulae.

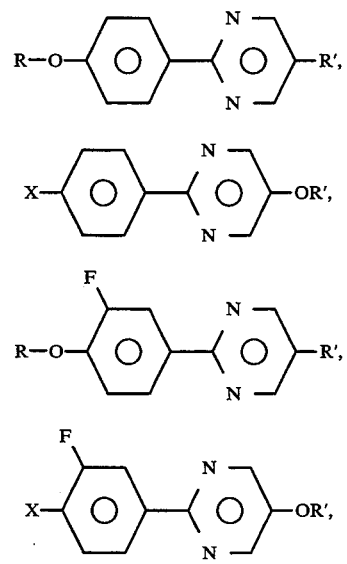

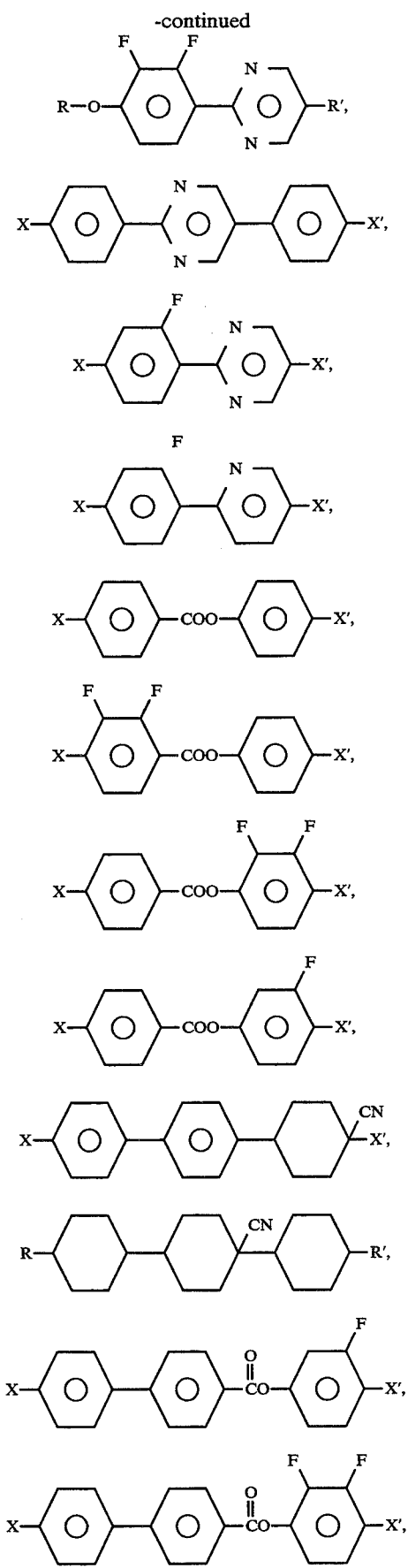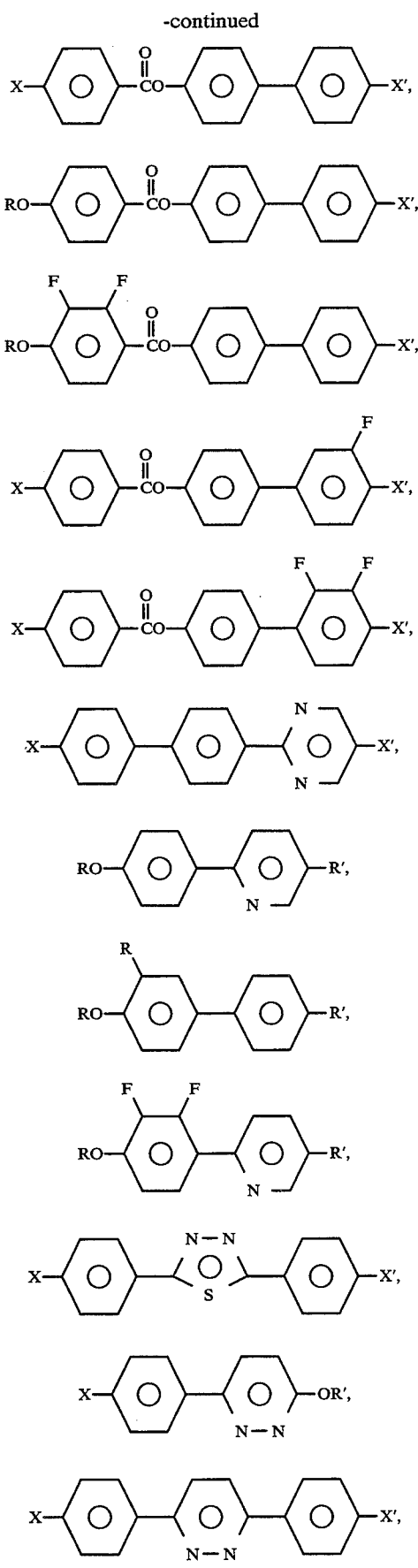

-continued

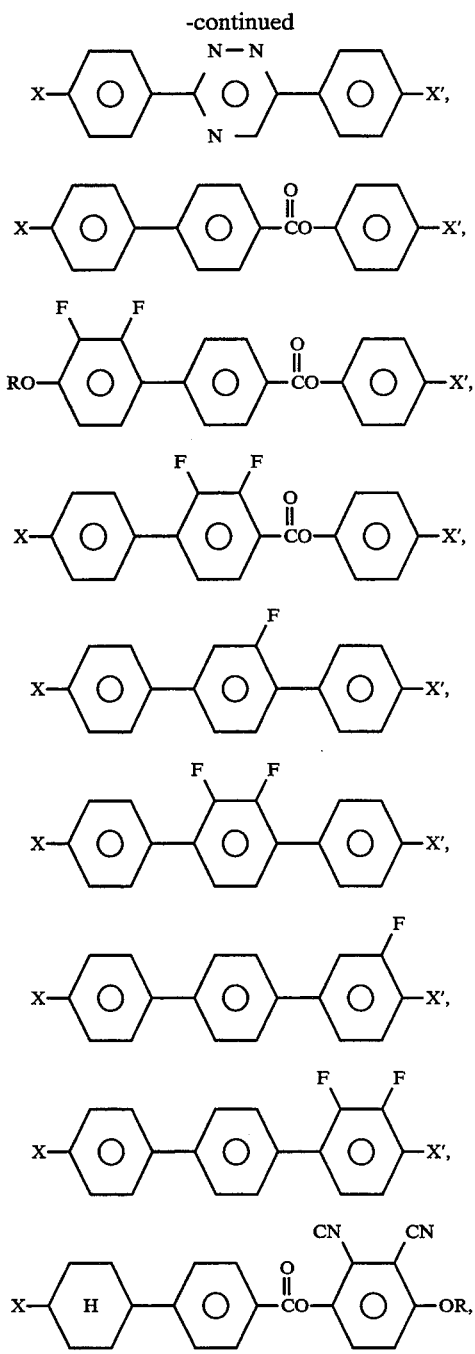

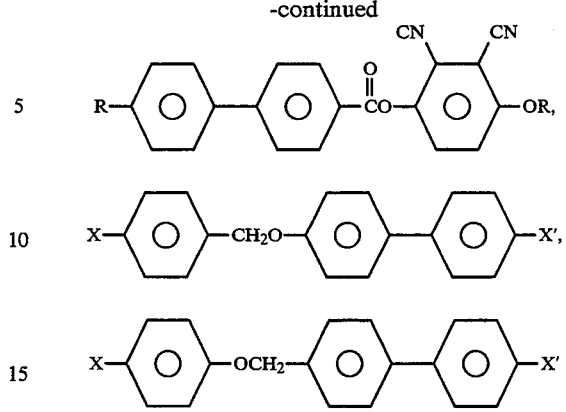

in which R and R' are each, independently of one another, alkyl having 5 to 18 carbon atoms and X and X' are each, independently of one another, alkyl, alkoxy, polyfluoroalkyl or polyfluoroalkoxy having 5 to 18 carbon atoms.

The phases according to the invention are prepared in a manner conventional per se. In general, the components are dissolved in one another, expediently at elevated temperature.

By means of suitable additives, the liquid-crystalline phases of the invention can be modified so that they can be used in all types of liquid-crystalline display elements which have been disclosed hitherto, in particular of the SSFLC type in the chevron or bookshelf geometry.

In the foregoing and in the following examples, all temperatures are set forth uncorrected in degrees Celsius; and, unless otherwise indicated, all parts and percentages are be weight. Also, m.p.=melting point, c.p.=clearing point. "Conventional work-up" means that water is added, the mixture is extracted with dichloromethane, the phases are separated, the organic phase is dried and evaporated, and the product is purified by crystallization and/or chromatography.

The entire disclosure of all applications, patents and publications, cited above and below, and of corresponding German application No. P 42 30 288.1, filed Sep. 10, 1992 is hereby incorporated by reference.

In the present application and in the examples below, the structures of the liquid-crystalline compounds are indicated by acronyms, the transformation into chemical formulae being carried out in accordance with Tables A and B below. All radicals $C_nH_{2n+1}$ and $C_mH_{2m+1}$ are straight-chain alkyl radicals having n and m carbon atoms, respectively. The coding in Table B is self-evident. In Table A, only the acronym for the parent structure is given. In individual cases, the acronym for the parent structure is followed, separated by a hyphen, by a code for the substituents $R^1$, $R^2$, $L^1$, $L^2$ and $L^3$:

| Code for $R^1$ $R^2$, $L^1$, $L^2$ | $R^1$ | $R^2$ | $L^1$ | $L^2$ | $L^3$ |
|---|---|---|---|---|---|
| nm | $C_nH_{2n+1}$ | $C_mH_{2m+1}$ | H | H | H |
| nOm | $C_nH_{2n+1}$ | $OC_mH_{2m+1}$ | H | H | H |
| nO.m | $OC_nH_{2n+1}$ | $C_mH_{2m+1}$ | H | H | H |
| nOOm | $OC_2H_{2n+1}$ | $OC_mH_{2m+1}$ | H | H | H |
| n | $C_nH_{2n+1}$ | CN | H | H | H |
| nN.F | $C_nH_{2n+1}$ | CN | H | F | H |
| nF | $C_nH_{2n+1}$ | F | H | H | H |
| nOF | $OC_nH_{2n+1}$ | F | H | H | H |
| nCl | $C_nH_{2n+1}$ | Cl | H | H | H |
| nF.F | $C_nH_{2n+1}$ | F | H | F | H |

-continued

| Code for $R^1$ $R^2$, $L^1$, $L^2$ | $R^1$ | $R^2$ | $L^1$ | $L^2$ | $L^3$ |
|---|---|---|---|---|---|
| nOmFF | $C_nH_{2n+1}$ | $OC_mH_{2m+1}$ | F | F | H |
| nmF | $C_nH_{2n+1}$ | $C_mH_{2m+1}$ | F | H | H |
| nCF$_3$ | $C_nH_{2n+1}$ | CF$_3$ | H | H | H |
| mOCF$_3$ | $C_nH_{2n+1}$ | OCF$_3$ | H | H | H |
| nOCF$_2$ | $C_nH_{2n+1}$ | OCHF$_2$ | H | H | H |
| nS | $C_nH_{2n+1}$ | NCS | H | H | H |
| rVsN | $C_rH_{2r+1}$—CH=CH—$C_sH_{2s}$— | CN | H | H | H |
| rEsN | $C_rH_{2r+1}$—O—$C_sH_{2s}$— | CN | H | H | H |
| nNF | $C_nH_{2n+1}$ | CN | F | H | H |
| nAm | $C_nH_{2n+1}$ | COOC$_m$H$_{2m+1}$ | H | H | H |
| nF.F.F | $C_nH_{2n+1}$ | F | H | F | F |
| nOCF$_3$.F | $C_nH_{2n+1}$ | OCF$_3$ | H | F | H |
| nOCF$_3$.F.F | $C_nH_{2n+1}$ | OCF$_3$ | H | F | F |
| nCl.F | $C_nH_{2n+1}$ | Cl | H | F | H |
| nCl.F.F | $C_nH_{2n+1}$ | Cl | H | F | F |

TABLE A

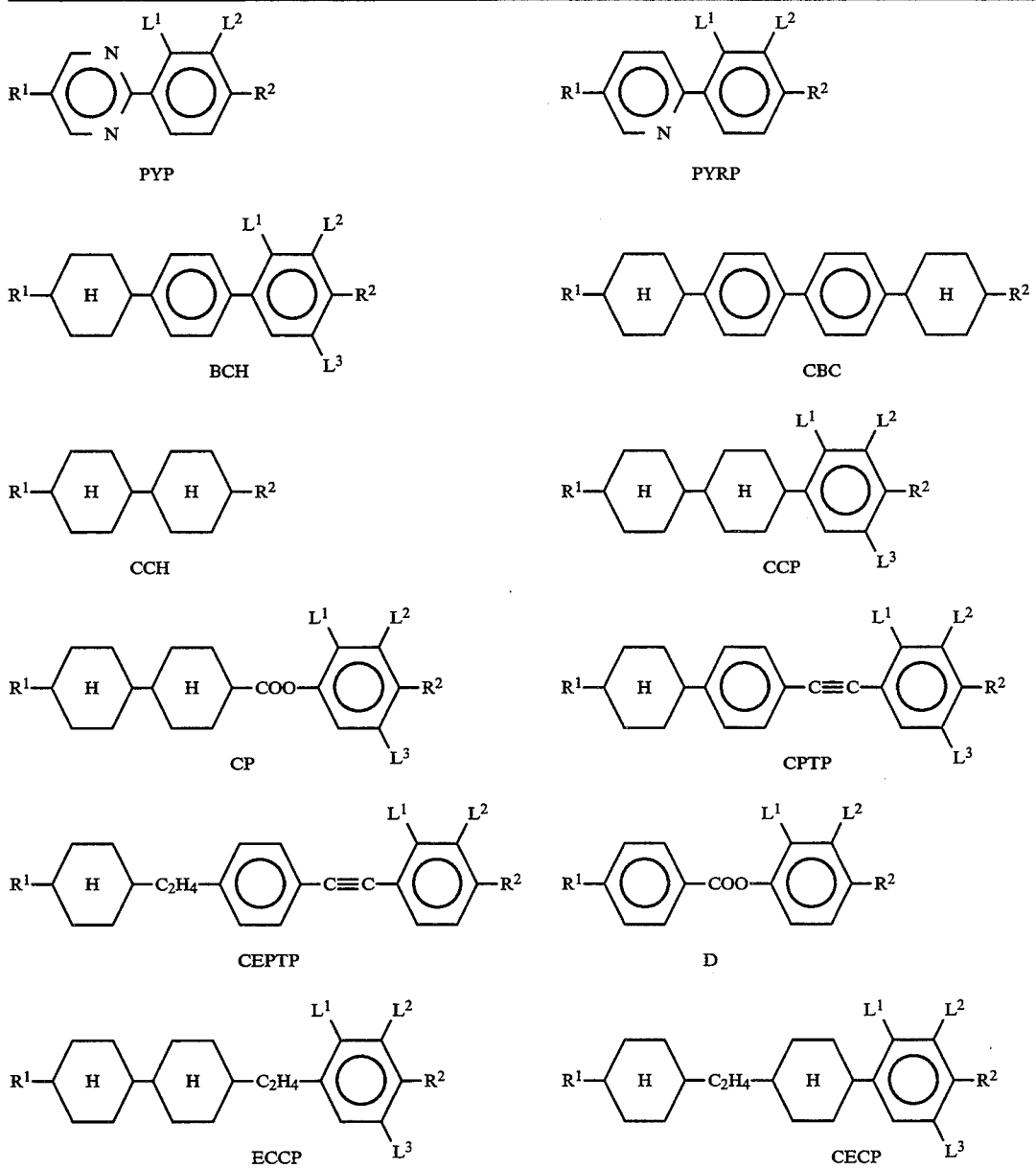

TABLE A-continued
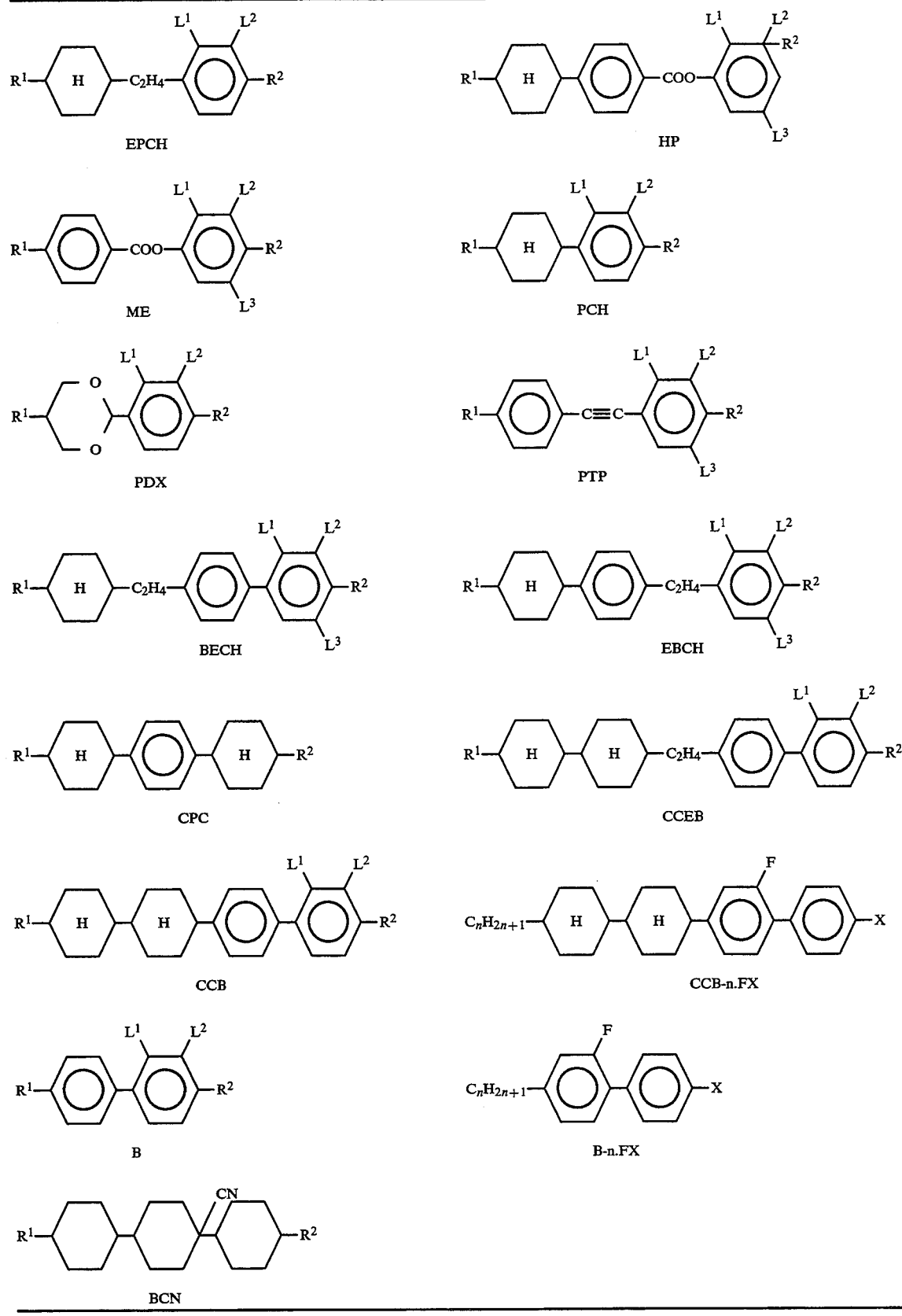

TABLE B
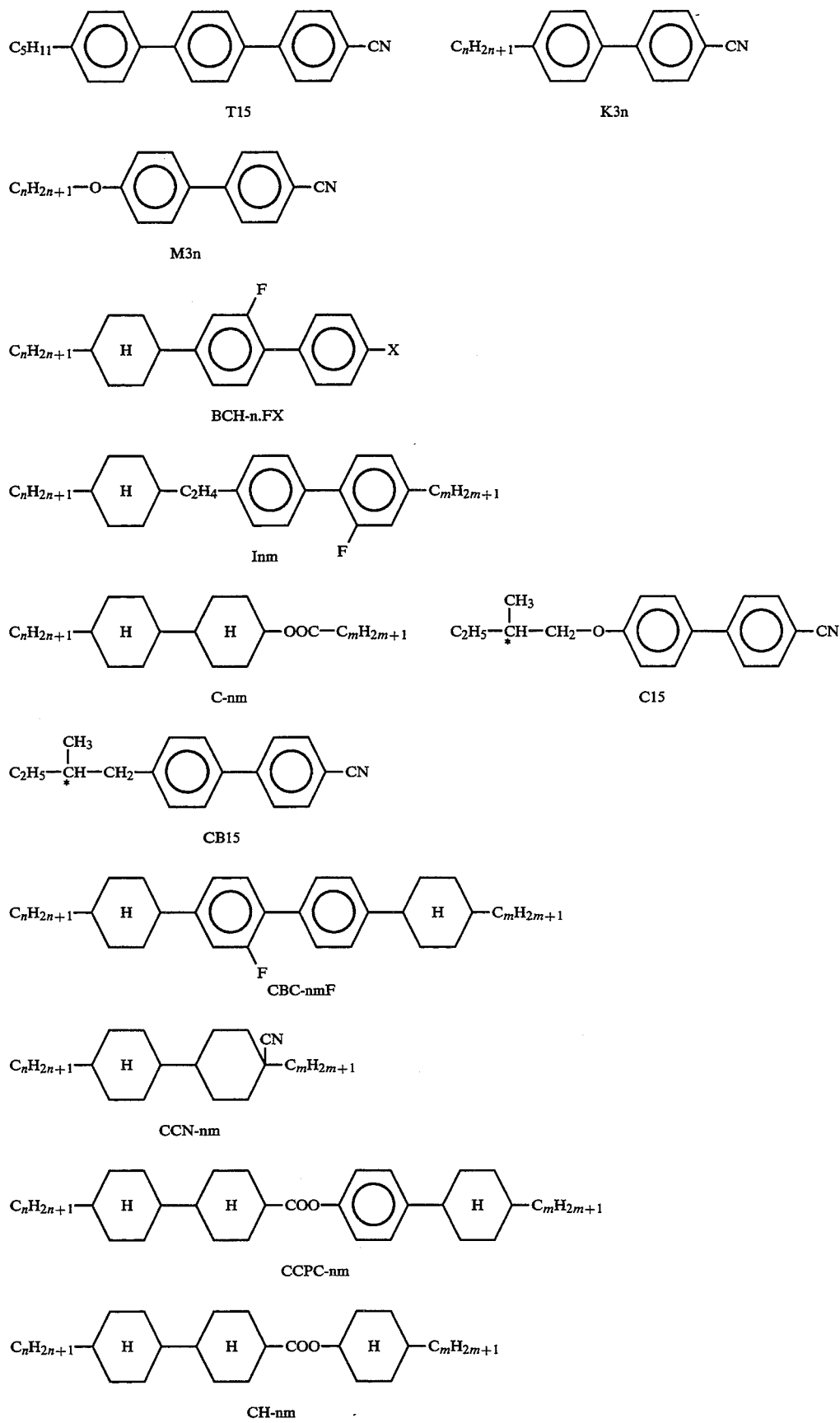

TABLE B-continued
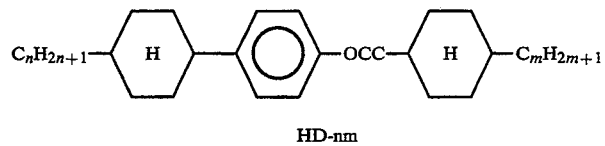
HD-nm
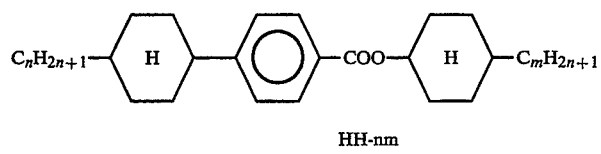
HH-nm
NCB-nm
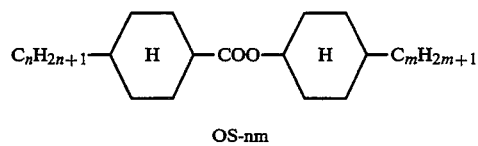
OS-nm
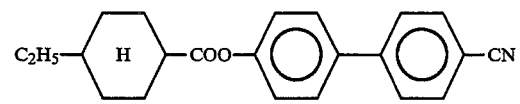
CHE
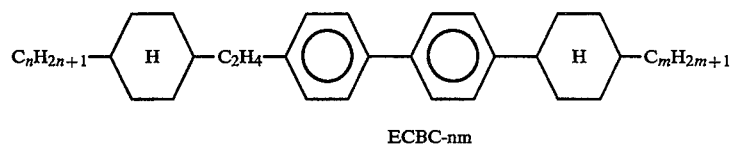
ECBC-nm
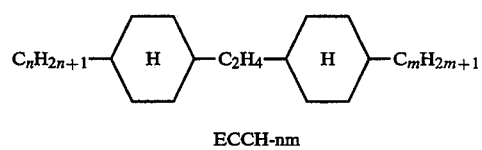
ECCH-nm
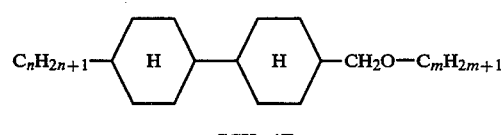
CCH-n1Em
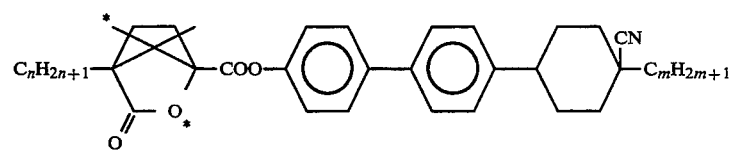
Val-NCB-nm
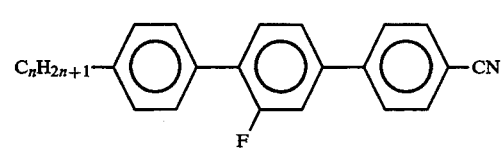
T-nFN

TABLE B-continued

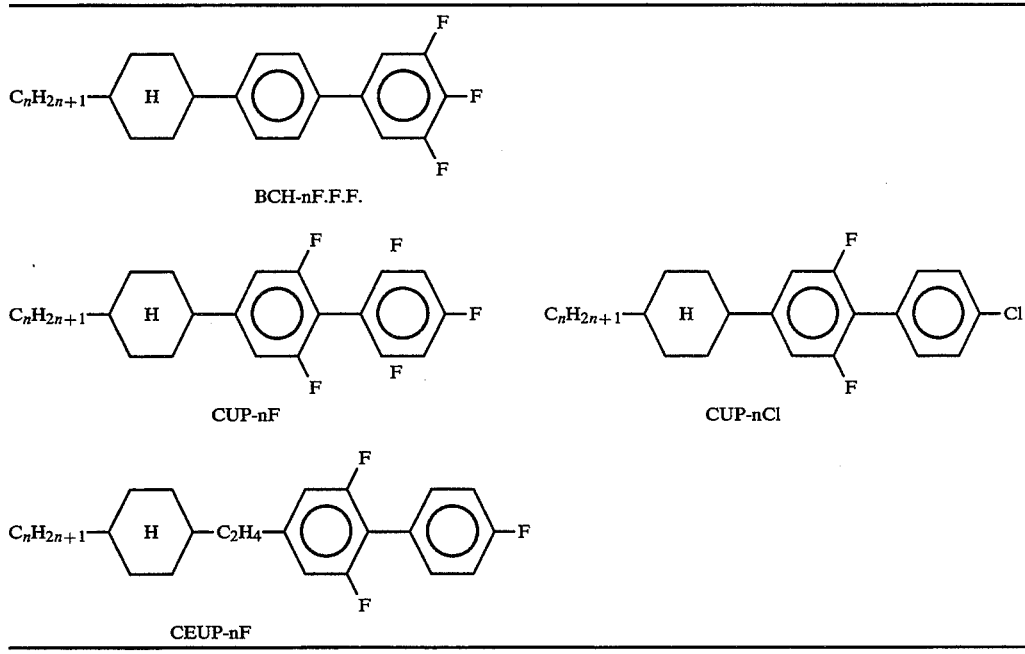

In addition, the following abbreviations are used:
DEAD: Diethyl azodicarboxylate, C: Crystalline solid state, S: Smectic phase (the index denotes the phase type), N: Nematic state, Ch: Cholesteric phase, I: Isotropic phase. The number between two symbols indicates the conversion temperature in degrees Celsius. $P_s$: Spontaneous polarisation, $\tau$: Response time.

EXAMPLE 1

A suspension of 6 mmol of camphanic chloride in 10 ml of toluene is added to a mixture of 6 mmol of 1-r-cyano-1-heptyl-cis-4-(4'-hydroxybiphenyl-4-yl)cyclohexane, 6 mmol of pyridine and 10 ml of toluene. The reaction mixture is heated at 100° C. for 1 hour, cooled to room temperature and poured into 50 ml of water.

Extraction with methyl tert-butyl ether, drying over magnesium sulfate, evaporation on a rotary evaporator and recrystallisation from ethanol/ethyl acetate ($\frac{1}{2}$) gives a pure product (Val-NCB-17) of the formula

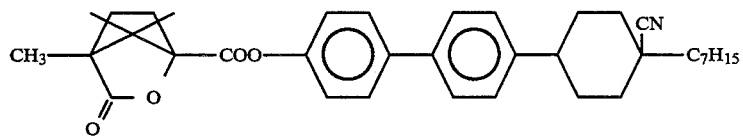

having C 153 Ch 151 I.

The compounds of the formula

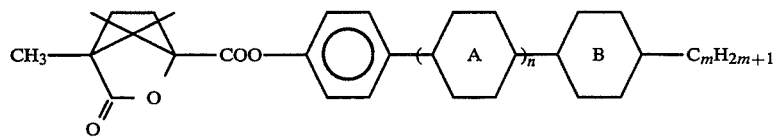

are prepared analogously:

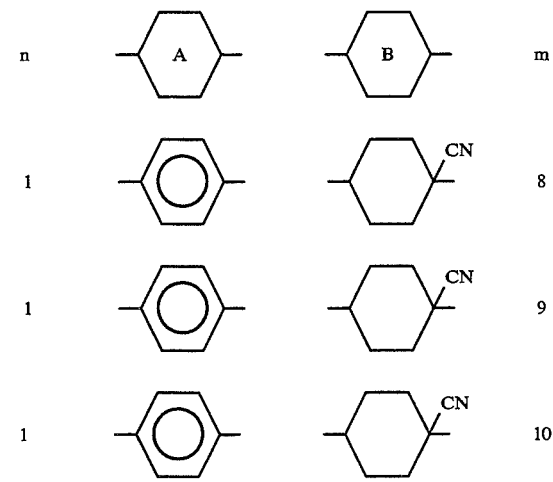

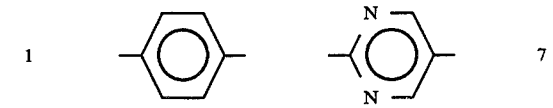

-continued

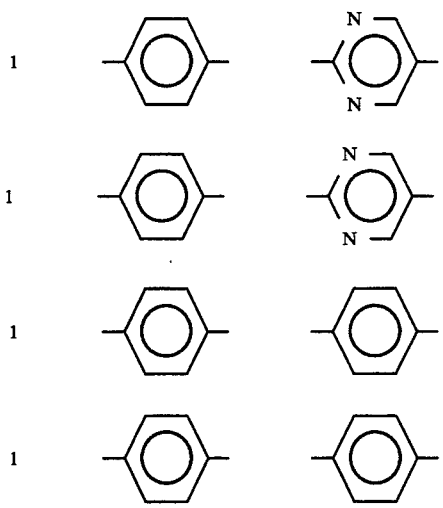

| | | |
|---|---|---|
| 1 | | 9 |
| 1 | | 11 |
| 1 | | 7 |
| 1 | | 8 |

Use Example 1

A liquid-crystalline base material (BM 1) having a broad $S_c$ phase is prepared, which comprises:

| | |
|---|---|
| PYP-706 | 3.3% |
| PYP-707 | 3.3% |
| PYP-708 | 3.3% |
| PYP-709 | 3.3% |
| PYP-906 | 7.8% |
| PYP-909 | 25.6% |
| NCB-804 | 31.1% |
| NCB-76 | 15.6% |
| BCN-55 | 6.7% |

This base material has the following phase transitions:
C<0 $S_c$ 76 $S_A$ 80 N 96 I
10% of the novel dope Val-NCB-17 are added.
The resultant ferroelectric medium has the following properties:
C<−10 $S_c^*$ 73 $S_A$ 79 Ch 99 I
$P_s$ (20° C.): 30.8 nC. cm$^{-2}$
$\tau$(20° C.): 115 $\mu$s (at 15 V/$\mu$m)
Helical pitch in the cholesteric phase:>40 $\mu$m
Tilt angle (20° C.): 30°

Use Example B

A liquid-crystalline base material (BM 2) having a broad $S_c$ phase is prepared, which comprises:

| | |
|---|---|
| PYP-907 | 20.00% |
| PYP-908 | 20.00% |
| PYP-909 | 20.00% |
| PYP-907FF | 6.67% |
| PYP-908FF | 6.67% |
| PYP-909FF | 6.67% |
| PYP-6006 | 20.00% |

BM 2 has the following phase transitions:
C 5 $S_c$ 64 $S_A$ 70 N 74 I
10% of the novel dope Val-NCB-17 are added. The resultant ferroelectric medium has the following properties:
$S_c^*$ 62 $S_A$ 68 Ch 72 I
Ps (20° C.) 16.9 nClcm$^{-2}$
$\tau$(20° C.) 51 $\mu$s (at 15 V/$\mu$m)
Tilt angle (20° C.) 25.5°

We claim:
1. A chiral valerolactone derivative of formula I

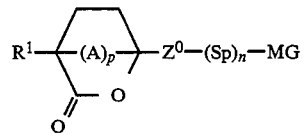

wherein
R$^1$ is C$_{1-18}$-alkyl in which one or two non-adjacent —CH$_2$ groups are optionally replaced by —O—, —CO—O—, —O—CO— or —S—,
A is —CH$_2$—, —C—(CH$_3$)$_2$— or —CH$_2$CH$_2$—,
Sp is a spacer, which optionally contains a chiral carbon atom,
Z$^0$ is —COO—, —CH$_2$O—, —CH$_2$CH$_2$—, —C≡C— or —CH=CH—,
n and p are each 0 or 1, and
MG is a radical of the formula II

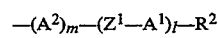

wherein
R$^2$ is C$_{1-18}$-alkyl or C$_{2-18}$-alkenyl optionally substituted by halogen or monosubstituted by cyano and in which one or two non-adjacent —CH$_2$—, groups are optionally replaced by —O—, —CO—O—, —O—CO— or —S—,
or R$^2$ is a radical of the formula

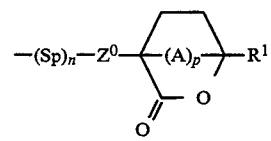

in which
A$^1$ and A$^2$ are each, independently of one another, 1,4-phenylene which is optionally substituted by one or two fluorine atoms and in which one or two CH groups are optionally replaced by N; 1,4-cyclohexylene which is optionally substituted by a cyano group and in which is optionally substituted by a cyano group and in which one or two CH$_2$ groups are optionally replaced by O or S; thiadiazole-2,5-diyl or 1,4-bicyclo[2,2,2]octylene;
Z$^1$ is —CO—O, —O—CO—, —CH$_2$O—, —OCH$_2$—, —CH$_2$CH$_2$—, —C≡C— or a single bond,
l is 0, 1 or 2,
m is 1 or 2, and
(l+m) is 1, 2 or 3.
2. A chiral valerolactone derivative according to claim 1, wherein Z$^0$ is —COO—.
3. A chiral valerolactone derivative according to claim 1, in which p is 1.
4. A chiral valerolactone derivative according to claim 1, wherein at least one of A$^1$ and A$^2$ is one of formula 1 to 7:

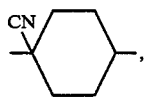 2

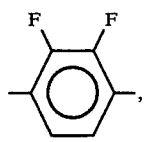 3

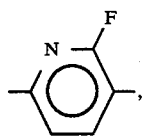 4

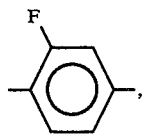 5

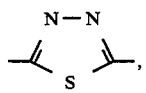 6

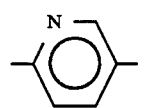 7

5. A chiral valerolactone derivative according to claim 1, in which Sp is a group of the formula III

 III wherein
q and s are each independently an integer between 0 and 6,
r is 0 or 1, and
W is halogen, $C_{1-6}$-alkyl or phenyl,
with the proviso that the sum of q, s and r is at least 1.

6. A chiral valerolactone derivative according to claim 5, in which Sp is a group of the formula III1

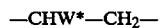 III1.

7. A chiral valerolactone derivative of formula I1

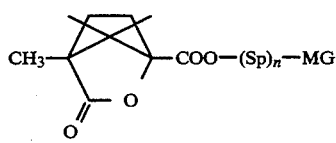 I1 wherein
Sp is a spacer, which optionally contains a chiral carbon atom,
n is 0 or 1, and
MG is a radical of the formula II

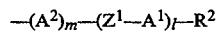 II wherein
$R^2$ is $C_{1-18}$-alkyl or $C_{2-18}$-alkenyl optionally substituted by halogen or monosubstituted by cyano and in which one or two non-adjacent —$CH_2$—, groups are optionally replaced by —O—, —CO—O—, —O—CO— or —S—,
or $R^2$ is a radical of the formula

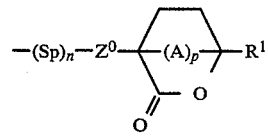

in which
$A^1$ and $A^2$ are each, independently of one another, 1,4-phenylene which is optionally substituted by one or two fluorine atoms and in which one or two CH groups are optionally replaced by N; 1,4-cyclohexylene which is optionally substituted by a cyano group and in which is optionally substituted by a cyano group and in which one or two $CH_2$ groups are optionally replaced by O or S; thiadiazole-2,5-diyl or 1,4-bicyclo[2,2,2]octylene;
$Z^1$ is —CO—O, —O—CO—, —$CH_2$O—, —O$CH_2$—, —$CH_2CH_2$—, —C≡C— or a single bond,
l is 0, 1 or 2,
m is 1 or 2,
(l+m) is 1, 2 or 3,
$Z^0$ is —COO—, —$CH_2$O—, —$CH_2CH_2$—, —C≡C— or —CH≡CH—,
$R^1$ is $C_{1-18}$-alkyl in which one or two non-adjacent —$CH_2$ groups are optionally replaced by —O—, —CO—O—, —O—CO— or —S—,
A is —$CH_2$—, —C—$(CH_3)_2$— or —$CH_2CH_2$—, and
p is 0 or 1.

8. A chiral valerolactone derivative of formula I1

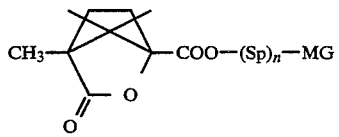 I1 wherein
Sp is a spacer, which optionally contains a chiral carbon atom,
n is 0, and
MG is a radical of the formula II

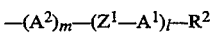 II wherein
$R^2$ is $C_{1-18}$-alkyl or $C_{2-18}$-alkenyl optionally substituted by halogen or monosubstituted by cyano and in which one or two non-adjacent —$CH_2$—, groups are optionally replaced by —O—, —CO—O—, —O—CO— or —S—,
or $R^2$ is a radical of the formula

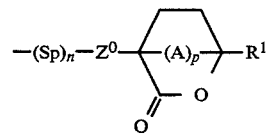

in which $A^1$ and $A^2$ are each, independently of one another, 1,4-phenylene which is optionally substituted by one or two fluorine atoms and in which one or two CH groups are optionally replaced by N; 1,4-cyclohexylene which is optionally substituted by a cyano group and in which is optionally substituted by a cyano group and in which one or two $CH_2$ groups are optionally replaced by O or S; thiadiazole-2,5-diyl or 1,4-bicyclo[2,2,2]octylene;

$Z^1$ is —CO—O—, —O—CO—, —CH$_2$O—, —OCH$_2$—, —CH$_2$CH$_2$—, —C≡C— or a single bond, l is 0, 1 or 2, m is 1 or 2, (l+m) is 1, 2 or 3, $Z^0$ is —COO—, —CH$_2$O—, —CH$_2$CH$_2$—, —C≡C— or —CH=CH—, $R^1$ is $C_{1-18}$ alkyl in which one or two non-adjacent —CH$_2$ groups are optionally replaced by —O—, —CO—O—, —O—CO— or —S—, A is —CH$_2$—, —C—(CH$_3$)$_2$— or —CH$_2$CH$_2$—, and p is 0 or 1.

9. A chiral valerolactone derivative of formula I

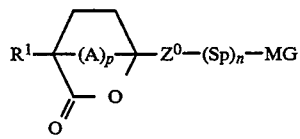

I wherein $R^1$ is $C_{1-18}$-alkyl in which one or two non-adjacent —CH$_2$ groups are optionally replaced by —O—, —CO—O—, —O—CO— or —S—, A is —CH$_2$—, —C—(CH$_3$)$_2$— or —CH$_2$CH$_2$—, Sp is a spacer, which optionally contains a chiral carbon atom, $Z^0$ is —COO—, —CH$_2$O—, —CH$_2$CH$_2$—, —C≡C— or —CH=CH—, n is 0, p is 0 or 1, MG is a radical of the formula II $$-(A^2)_m-(Z^1-A^1)_l-R^2$$  II wherein $R^2$ is $C_{1-18}$-alkyl or $C_{2-18}$-alkenyl optionally substituted by halogen or monosubstituted by cyano and in which one or two non-adjacent —CH$_2$—, groups are optionally replaced by —O—, —CO—O—, —O—CO— or —S—, or $R^2$ is a radical of the formula

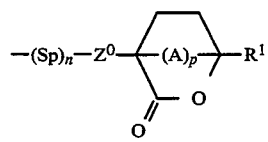

in which $A^1$ and $A^2$ are each, independently of one another, 1,4-phenylene which is optionally substituted by one or two fluorine atoms and in which one or two CH groups are optionally replaced by N; 1,4-cyclohexylene which is optionally substituted by a cyano group and in which is optionally substituted by a cyano group and in which one or two $CH_2$ groups are optionally replaced by O or S; thiadiazole-2,5-diyl or 1,4-bicyclo[2,2,2]octylene;

$Z^1$ is —CO—O—, —O—CO—, —CH$_2$O—, —OCH$_2$—, —CH$_2$CH$_2$—, —C≡C— or a single bond, l is 0, 1 or 2, m is 1 or 2, and (l+m) is 1, 2 or 3.

* * * * *